US008241232B2

(12) United States Patent
Sanders

(10) Patent No.: US 8,241,232 B2
(45) Date of Patent: Aug. 14, 2012

(54) FOOT PAIN RELIEF DEVICE

(76) Inventor: Jeannie B. Sanders, Forrest, IL (US)

(*) Notice: Subject to any disclaimer, the term of this patent is extended or adjusted under 35 U.S.C. 154(b) by 542 days.

(21) Appl. No.: 12/548,324

(22) Filed: Aug. 26, 2009

(65) Prior Publication Data

US 2011/0054368 A1 Mar. 3, 2011

(51) Int. Cl.

| | |
|---|---|
| *A61H 1/00* | (2006.01) |
| *A61H 7/00* | (2006.01) |
| *A61H 15/00* | (2006.01) |
| *A63B 23/08* | (2006.01) |
| *A63B 21/00* | (2006.01) |
| *A63B 21/02* | (2006.01) |
| *A63B 21/045* | (2006.01) |
| *A63B 7/00* | (2006.01) |
| *A63B 22/14* | (2006.01) |
| *A63B 23/00* | (2006.01) |
| *A43B 3/12* | (2006.01) |
| *A43B 13/28* | (2006.01) |
| *A43B 13/18* | (2006.01) |
| *A43B 13/38* | (2006.01) |
| *A43B 23/00* | (2006.01) |
| *A61F 5/14* | (2006.01) |

(52) U.S. Cl. .............. 601/124; 601/23; 601/27; 601/28; 601/29; 601/30; 601/31; 601/32; 601/33; 601/84; 601/112; 601/113; 601/115; 601/118; 601/119; 601/120; 601/125; 601/132; 601/134; 601/135; 601/136; 601/137; 482/79; 482/80; 482/92; 482/121; 482/126; 482/127; 482/131; 482/132; 482/139; 482/146; 482/147; 482/148; 36/11.5; 36/27; 36/28; 36/43; 36/44; 36/136; 36/141

(58) Field of Classification Search .................... 601/23, 601/27–33, 84, 112, 113, 115, 118–120, 601/124, 125, 132, 134–137; 482/79, 80, 482/92, 121, 126, 127, 131, 132, 139, 146, 482/147, 148; 36/11.5, 27, 28, 43, 44, 136, 36/141

See application file for complete search history.

(56) References Cited

U.S. PATENT DOCUMENTS

| | | | |
|---|---|---|---|
| 5,087,036 | A | 2/1992 | Cooper |
| 5,399,155 | A | 3/1995 | Strassburg et al. |
| 6,110,078 | A | 8/2000 | Dyer |

*Primary Examiner* — Patricia Bianco
*Assistant Examiner* — Nihir Patel
(74) *Attorney, Agent, or Firm* — Bever, Hoffman & Harms, LLP; Jeanette S. Harms

(57) ABSTRACT

A foot pain relief device can advantageously provide multiple angles of inclination, directed pressure against the plantar fascia, as well as ease of manufacturing and assembly. A toe strap, which is fastened around the ankle and the toe(s), ensures that the toes are flexed up. This toe flexing tenses the plantar fascia of the foot. A ball strap can be threaded through a hole in a ball and then operatively coupled with the toe strap. When operatively coupled to the toe strap, the ball strap keeps the ball positioned on the bottom of the foot while allowing ball mobility. The mobility of the ball can provide directed pressure on at least one component of the plantar fascia. Notably, the simultaneous combination of tension to the plantar fascia and directed pressure to the component(s) of the plantar fascia can be particularly effective at relieving foot pain.

7 Claims, 3 Drawing Sheets

FOOT PAIN RELIEF DEVICE

BACKGROUND OF THE INVENTION

1. Field of the Invention

The present invention relates to a device designed to minimize pain associated with the plantar fascia.

2. Related Art

The plantar fascia is a fibrous connective tissue that supports the arch of a foot. FIG. 1 illustrates a simplified diagram of a plantar fascia 100. As shown, the plantar fascia 100 extends from the proximal phalanges 102 of the toes to the calcaneal tuberosity 103 of the heel. The plantar fascia 100 includes three major components: the central component 101, the lateral component 104, and the medial component 105. Chronic overstressing of the plantar fascia can lead to inflammation, tearing, and/or shortening of this tissue. The resulting condition is called plantar fasciitis, which can cause severe foot pain. Although the central component 101 of the plantar fascia is generally considered the primary source of plantar fasciitis, both the lateral component 104 and the medial component 105 can also contribute to this painful foot ailment.

Various devices have been proposed to alleviate the pain associated with plantar fasciitis. For example, U.S. Pat. No. 6,110,078, issued to Dyer on Aug. 29, 2000, teaches positioning the heel of the foot at the "V" of two hinged plates and securing the foot in this position to one of the hinged plates using a strap. A spring and cinching device, which are attached to the open ends of the two plates, can then be pulled together to increase tension in the plantar fascia. An optional arch support and toe support can be provided to enhance the stretch of the plantar fascia.

The Dyer stretching device has several significant disadvantages. For example, the toe support provides a single angle of inclination, thereby ignoring the difference in flexibility of peoples' toes. Moreover, the arch support is in a fixed position, and therefore provides only general pressure against the plantar fascia. Yet further, the stretching device has many components, thereby undesirably increasing manufacturing cost and complexity of assembly.

U.S. Pat. No. 5,087,036, issued to Cooper on Feb. 11, 1992, partially solves the fixed toe support problem by providing a foot plate on which the heel and ball of the foot rests. An adjustable toe plate, on which the toes of the foot rest, is hinged to the foot plate. A support arm, which is pivotably attached to the toe plate, can engage with a selected groove in the foot plate to position the toes at an inclined angle.

The Cooper stretching device also has several significant disadvantages. For example, to achieve maximum benefit from the device, a user must be standing. Moreover, although the plantar fascia is under tension when the foot is positioned in the device, no pressure is provided on the plantar fascia by the device.

U.S. Pat. No. 5,399,155, issued to Strassburg et al. on Mar. 21, 1995, teaches a sock that includes an inelastic reinforcing strap and a "D" ring that are positioned approximately at mid-shin above the user's calf. A second, tapered inelastic strap is attached to the toe end of the sock. A hook and loop assembly, which is attached to the opposite end of the tapered inelastic strap, can be pulled through the "D" ring and then secured at the desired angle of toe inclination.

Although providing flexibility of toe inclination, the Strassburg stretching device still has several disadvantages. For example, the user must put a sock, which may be inconvenient. Moreover, the sock must be periodically washed, thereby requiring regular user maintenance. Yet further, although the plantar fascia is under tension when the hook and loop assembly is secured in the device, no pressure is provided on the plantar fascia by the device.

Therefore, what is needed is a device that can provide multiple angles of inclination, directed pressure against the plantar fascia, as well as ease of manufacturing and assembly.

SUMMARY OF THE INVENTION

A foot pain relief device can advantageously provide multiple angles of inclination, directed pressure against the plantar fascia, as well as ease of manufacturing and assembly. The foot pain relief device can include a first strap, a second strap, and a ball.

The first strap can be fastened around an ankle and at least one toe of a foot. The fastened length of the first strap is adjustable to ensure that the at least one toe is flexed up. This toe flexing can tense the plantar fascia of the user's foot.

The second strap can be threaded through a hole in the ball, wherein the second strap operatively couples with the first strap. When operatively coupled with the first strap, the second strap facilitates keeping the ball positioned on the bottom of the foot while allowing ball mobility. Advantageously, the mobility of ball can provide directed pressure on at least one component of the plantar fascia.

Notably, the simultaneous combination of tension to the plantar fascia (provided by the first strap) and directed pressure to one or more components of the plantar fascia (provided by the ball and second strap), which creates yet further stretching of one or more specific components the plantar fascia, can be particularly effective at relieving foot pain.

In one embodiment, at least one of the first strap and the second strap includes a hook/loop fastener. An exemplary hook/loop fastener is Velcro. In one embodiment, at least one of the first strap and the second strap consists essentially of double-sided Velcro. In another embodiment, the first strap includes ends with a hook/loop fastener, and the second strap includes looped ends for receiving the first strap. In yet another embodiment, the second strap consists essentially of an elastic material and includes looped ends for receiving the first strap. In yet another embodiment, the first strap includes at least one snap fastener, each snap fastener having a male member on one end of the first strap and a female member on another end of the first strap. In one embodiment, to provide the desired pressure/stretching, the ball can be formed from a rigid or semi-rigid material

DETAILED DESCRIPTION OF THE DRAWINGS

Figure 2:
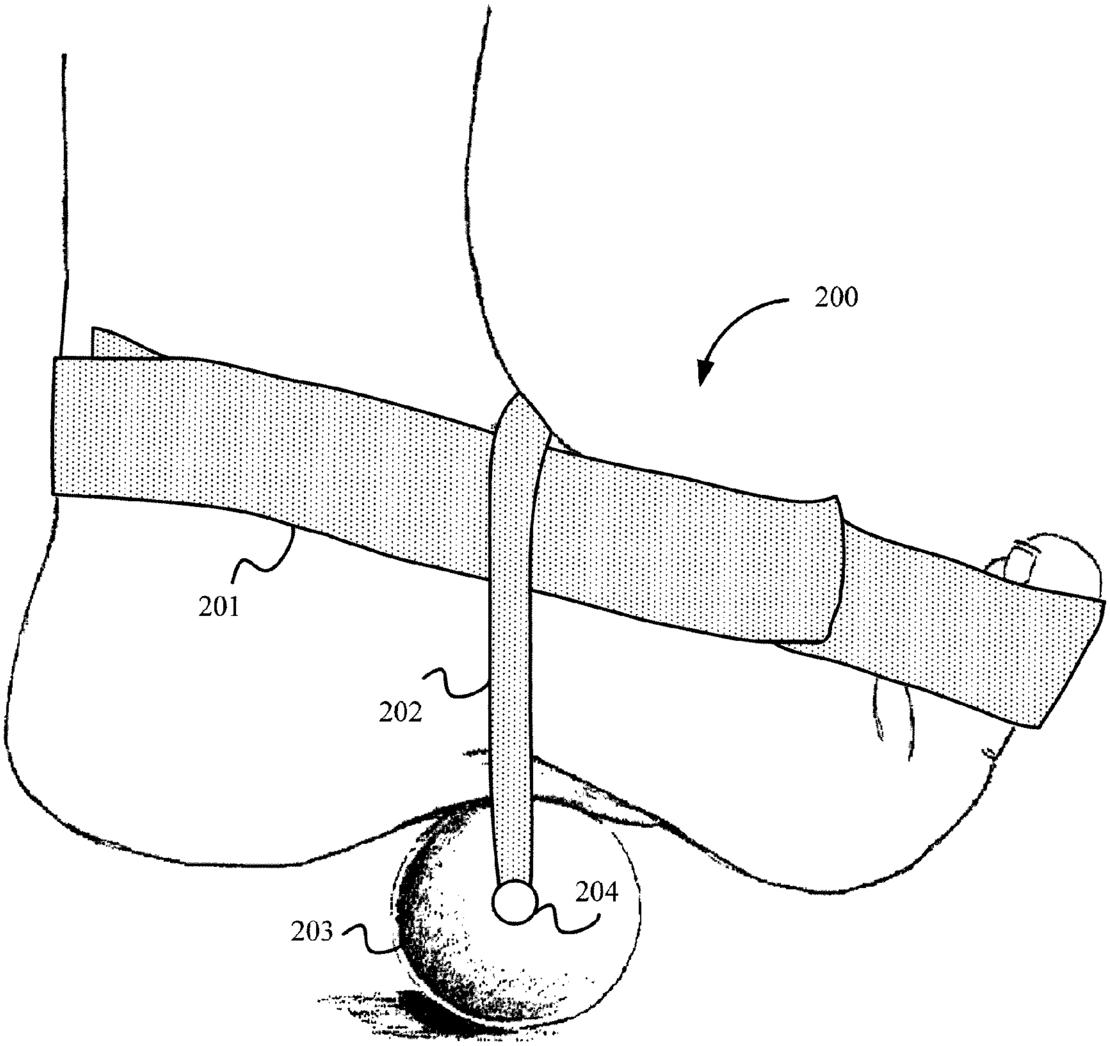
FIG. 2 illustrates an exemplary embodiment of a foot pain relief device in accordance with the invention.

FIG. 2 illustrates an exemplary embodiment of a foot pain relief device 200 that can provide multiple angles of inclination, directed pressure against the plantar fascia, as well as ease of manufacturing and assembly. The foot pain relief device 200 can include a toe strap 201, a ball strap 202, and a ball 203.

The toe strap 201 can be used to wrap around one or more toes (at least the big toe) and the ankle to keep the toe(s) in a flexed position. For example, while sitting on a chair, a person can position the toe strap 202 around the desired number of toes and the ankle. In one embodiment, the toe strap 201 can wrap around the first three toes of the foot. The user can then gently stretch the toe(s) back (flexed up) while adjusting a fastened length of the toe strap 202 to provide the desired tension in the plantar fascia. In one embodiment, the toe strap 201 can consist essentially of double-sided Velcro, thereby maximizing the user's selection of toe inclination.

In one embodiment, the ball 203 has a hole 204 through which the ball strap 202 can be threaded. While sitting on a chair, a user can loosely fasten the ball strap 202 around the width of the foot while positioning the ball 203 under the arch of the foot. In one embodiment, the ball strap 202 can also consist essentially of double-sided Velcro, thereby allowing complete adjustability for foot size and maximizing ball mobility (described below).

Figure 1:
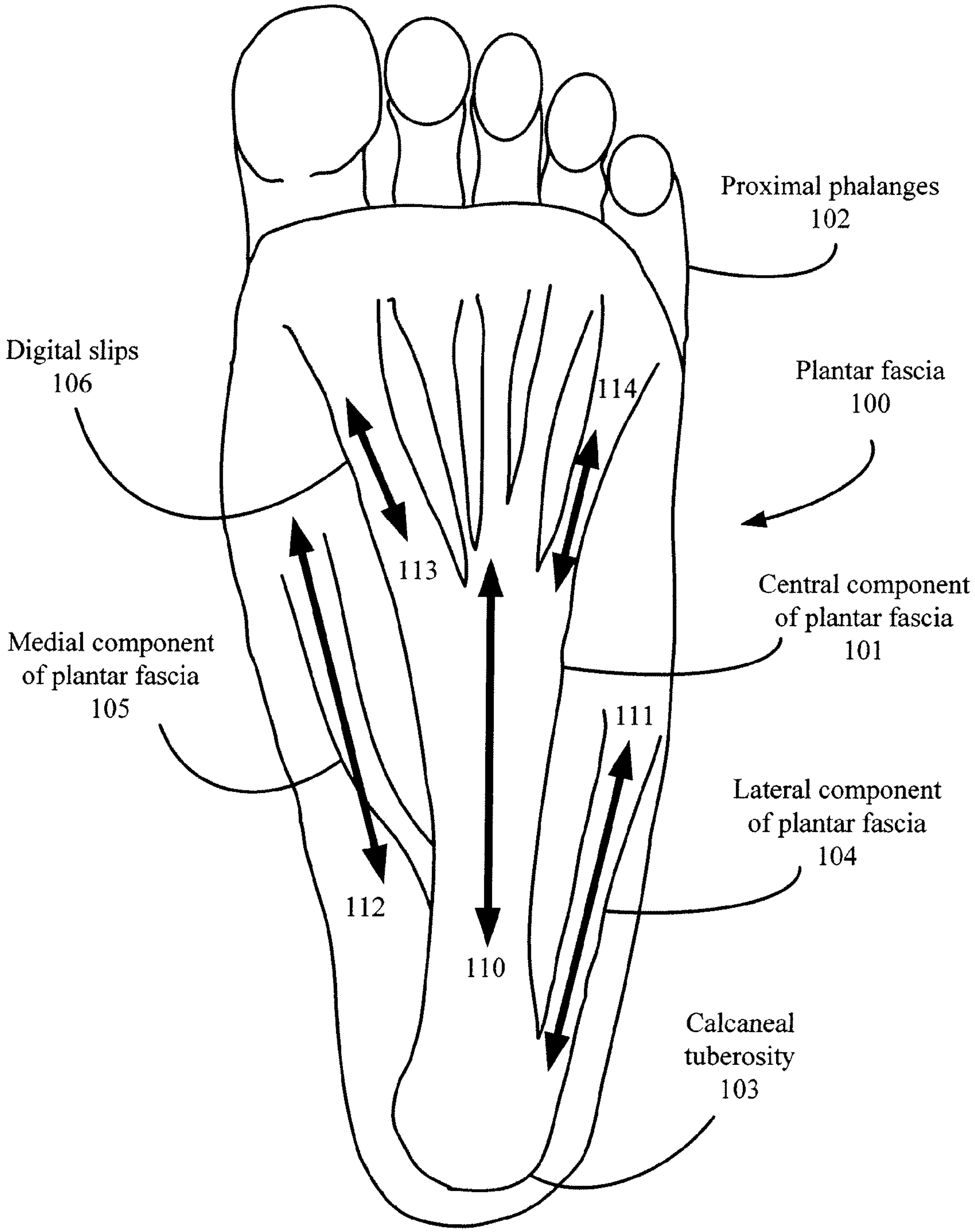
FIG. 1 illustrates the location of the plantar fascia in a foot.

In accordance with one aspect of the foot pain relief device 200, the toe strap 201 and the ball strap 202 can be operatively coupled to ensure that the ball 203 remains under the foot while still allowing mobility of the ball 203 in a rolling motion. Of importance, the rolling of the ball on the bottom of the foot can advantageously provide directed pressure on the plantar fascia. Specifically, referring back to FIG. 1, the user can gently roll the ball 203 against the bottom of the foot to put directed pressure on one or more components of the plantar fascia 100, e.g. the central component 101 (shown by arrow 110), the lateral component 104 (shown by arrow 111), the medial component 105 (shown by arrow 112), and even the digital slips 106 (shown by arrows 113 and 114). Notably, the simultaneous combination of tension to the plantar fascia (provided by the toe strap) and directed pressure to one or more components of the plantar fascia (provided by the ball and ball strap), which creates yet further stretching of one or more specific components the plantar fascia, is particularly effective at relieving foot pain. In one embodiment, to provide the desired pressure/stretching, the ball can be formed from a rigid or semi-rigid material, e.g. wood, rubber, etc.

Note that when both the toe strap 201 and the ball strap 202 are implemented with double-sided Velcro, the sides of the straps next to the foot are the same. That is, double-sided Velcro straps are fabricated to have one side that has tiny hooks and another side that has small loops. When the hooks side and the loop side are pressed together, the hooks catch the loops and hold the pieces together. Referring to FIG. 2, the toe strap 201 and the ball strap 202 when fastened around the foot in their respective orientations (i.e. one lengthwise on the foot and the other widthwise), should have the same sides touching the foot, thereby ensuring that opposite sides of the toe strap 201 and the ball strap 202 touch and couple. For example, if the loop side of toe strap 201 and the ball strap 202 are touching the foot, then the loop side of the ball strap 202 engages and couples to the hook side of the toe strap 201. Similarly, if the hook side of toe strap 201 and the ball strap 202 are touching the foot, then the hook side of the ball strap 202 engages and couples to the loop side of the toe strap 201.

Figure 3A:
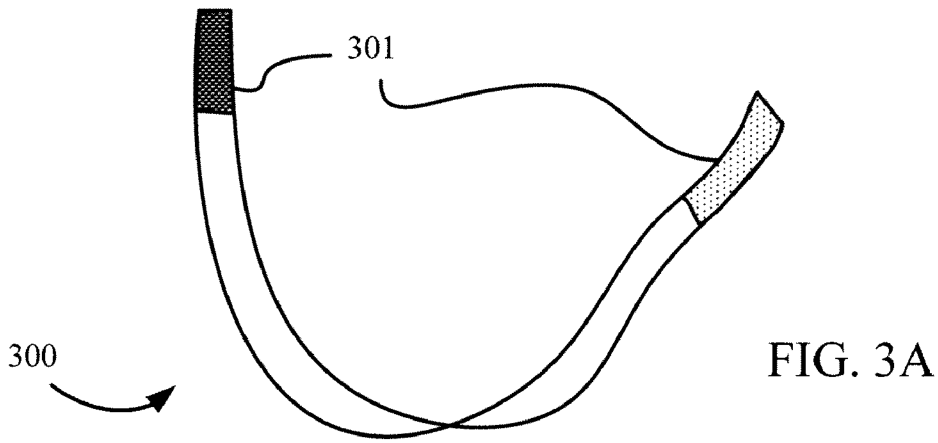
FIGS. 3A-3C illustrate exemplary straps usable in the described foot pain relief device.

Although double-sided Velcro can be used to implement the toe strap and the ball strap, other types of straps or a combination of different types of straps can be used in the described foot pain relief device. In one embodiment, at least one of the toe strap and the ball strap can include any type of hook/loop fastener. For example, referring to FIG. 3A, a toe strap 300 can be implemented with a hook/loop fastener 301 at its ends to form the fastened toe strap.

Figure 3B:
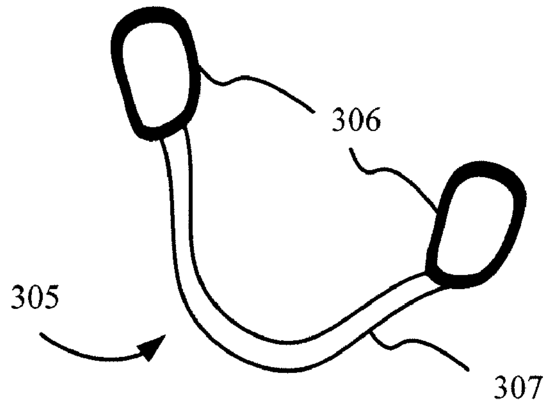

In this case and referring to FIG. 3B, to provide the operative coupling with the toe strap 300, a ball strap 305 can include loops 306 at the strap ends. In this configuration, the toe strap (e.g. the toe strap 300 shown in FIG. 3A) with the ball threaded thereon could be threaded through the loops 306 of the ball strap, thereby positioning the ball on the bottom of the foot. In one embodiment, the material for implementing the loops 306 can be a rigid or semi-rigid material, and the material for implementing the strap 307 can include a flexible material (e.g. elastic). The strap 307 can be attached to the loops 306 by stitching or any other manner of attachment. Note that implementing at least a portion of the ball strap with elastic can advantageously provide significant flexibility in accommodating different sizes of feet.

Figure 3C:
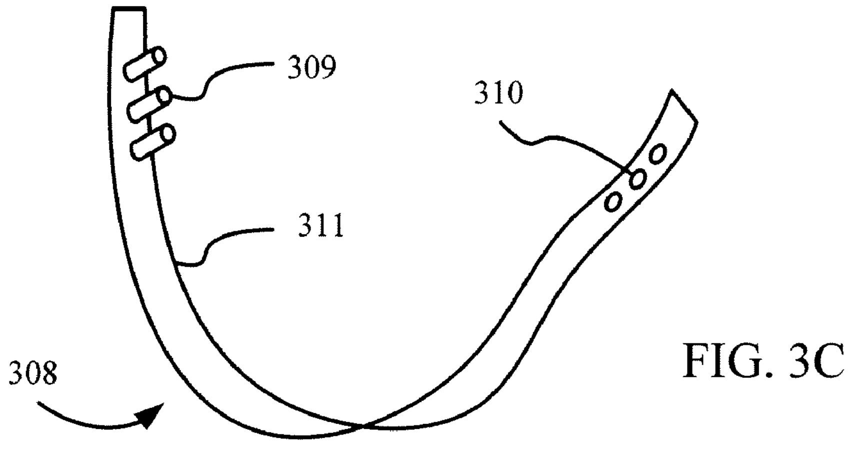

In yet another embodiment shown in FIG. 3C, a toe strap 308 can include snaps that have male members 309 that snap into female members 310 to form the fastened toe strap. Note that although toe strap 308 provides less adjustability than a hook/loop strap, providing more female members 310 can partially compensate for this limitation. In this embodiment, a ball strap similar to that shown in FIG. 3B can be used to achieve the operative coupling between the toe and ball straps. Note that toe strap 308 can be fabricating using any number of materials. For example, toe strap 308 and its snaps may be molded from a flexible plastic. In another embodiment, the strap 311 may be made from fabric, while the snaps (members 309/310) may be made from metal. Note that the snaps can be implemented using any style, e.g. post-style, prong-style, etc.

As described above, the foot pain relief device can include three elements: the toe strap, the ball strap, and the ball. These elements are easy to manufacture and assemble. Advantageously, the foot pain relief device can be used with or without socks. Moreover, the foot pain relief device can be used while sitting down or even when lying down (as long as a surface on which for rolling the ball is available). Yet further, the foot pain relief device requires no maintenance. Note that the toe strap, the ball strap, and/or the ball may have various logos, designs, or lettering provided on or embedded within their materials of construction. These elements are non-essential to the general functioning of the foot pain relief device and therefore are not discussed in detail herein.

Although illustrative embodiments have been described in detail herein with reference to the accompanying figures, it is to be understood that the invention is not limited to those precise embodiments. They are not intended to be exhaustive or to limit the invention to the precise forms disclosed. As such, many modifications and variations will be apparent to practitioners skilled in this art. For example, note that the toe strap, the ball strap, and the ball may be made from different materials than those described herein. Those materials, if providing/allowing the functionality described herein, are considered embodiments of the present invention. Further note that when the ball strap and the toe strap include hook/loop fasteners, the toe strap and the ball strap can be fastened in either order, i.e. toe strap then ball strap, or ball strap then toe strap.

Accordingly, it is intended that the scope of the invention be defined by the following Claims and their equivalents.

The invention claimed is:

1. A foot pain relief device comprising:

a first strap for fastening around an ankle and at least one toe of a foot, wherein a fastened length of the first strap is adjustable to ensure that the at least one toe is flexed up, thereby tensing a plantar fascia of the foot;

a ball having a hole therein, the ball for providing directed pressure on at least one component of the plantar fascia; and a second strap for threading through the hole in the ball, wherein the second strap is for operatively coupling with the first strap, wherein when operatively coupled with the first strap, the second strap facilitates keeping the ball positioned on a bottom of the foot while allowing ball mobility.

2. The foot pain relief device of claim 1, wherein at least one of the first strap and the second strap includes a hook/loop fastener.

3. The foot pain relief device of claim 1, wherein at least one of the first strap and the second strap consists essentially of a double-sided hook/loop fastener.

4. The foot pain relief device of claim 1, wherein the first strap includes ends with a hook/loop fastener.

5. The foot pain relief device of claim 1, wherein the first strap consists essentially of double-sided hook/loop fastener, and the second strap includes looped ends for receiving the first strap.

6. The foot pain relief device of claim 1, wherein the second strap consists essentially of an elastic material and includes looped ends for receiving the first strap.

7. The foot pain relief device of claim 1, wherein the first strap includes at least one snap fastener, each snap fastener having a male member on one end of the first strap and a female member on another end of the first strap.

* * * * *